US006773261B2

(12) United States Patent
Craig et al.

(10) Patent No.: US 6,773,261 B2
(45) Date of Patent: Aug. 10, 2004

(54) PROCESSES FOR FORMING DENTAL MATERIALS

(75) Inventors: Bradley D. Craig, Cottage Grove, MN (US); Rajdeep S. Kalgutkar, St. Paul, MN (US); Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 223 days.

(21) Appl. No.: 10/185,436

(22) Filed: Jun. 28, 2002

(65) Prior Publication Data

US 2004/0002036 A1 Jan. 1, 2004

(51) Int. Cl.$^7$ .................................................. A61C 5/00
(52) U.S. Cl. ..................................... 433/228.1; 433/226
(58) Field of Search ........................... 433/29, 215, 216, 433/217.1, 226, 228.1

(56) References Cited

U.S. PATENT DOCUMENTS

| | | | |
|---|---|---|---|
| 4,292,152 A | | 9/1981 | Lechtken et al. |
| 4,298,738 A | | 11/1981 | Lechtken et al. |
| 4,324,744 A | | 4/1982 | Lechtken et al. |
| 4,356,296 A | | 10/1982 | Griffith et al. |
| 4,385,109 A | | 5/1983 | Lechtken et al. |
| 4,503,169 A | | 3/1985 | Randklev |
| 4,516,195 A | | 5/1985 | Gonser |
| 4,544,467 A | * | 10/1985 | Bunker et al. ................ 522/13 |
| 4,642,126 A | | 2/1987 | Zador et al. |
| 4,652,274 A | | 3/1987 | Boettcher et al. |
| 4,695,251 A | | 9/1987 | Randklev |
| 4,710,523 A | | 12/1987 | Lechtken et al. |
| 4,719,149 A | | 1/1988 | Aasen et al. |
| 4,737,593 A | | 4/1988 | Ellrich et al. |
| 4,872,936 A | | 10/1989 | Engelbrecht |
| 4,888,489 A | | 12/1989 | Bryan |
| 5,063,257 A | | 11/1991 | Akahane et al. |
| 5,076,844 A | | 12/1991 | Fock et al. |
| 5,110,513 A | | 5/1992 | Puvilland |
| 5,130,347 A | | 7/1992 | Mitra |
| 5,147,204 A | | 9/1992 | Patten et al. |
| 5,154,762 A | | 10/1992 | Mitra et al. |
| 5,227,413 A | | 7/1993 | Mitra |
| 5,256,447 A | | 10/1993 | Oxman et al. |
| 5,367,002 A | | 11/1994 | Huang et al. |
| 5,472,991 A | | 12/1995 | Schmitt et al. |

(List continued on next page.)

FOREIGN PATENT DOCUMENTS

| | | |
|---|---|---|
| DE | 2846471 A1 | 5/1980 |
| DE | 29714686 U1 | 12/1997 |
| DE | 10065903 A1 | 1/2002 |
| EP | 0173567 A2 | 3/1986 |
| EP | 0201031 B1 | 11/1986 |
| EP | 0201778 B1 | 11/1986 |
| EP | 0325266 B1 | 7/1989 |
| EP | 0325266 A2 | 7/1989 |
| EP | 0325266 A3 | 7/1989 |
| EP | 0373384 B1 | 6/1990 |
| WO | WO 99/22667 | 5/1999 |
| WO | WO 00/38619 | 7/2000 |
| WO | WO 00/42092 | 7/2000 |
| WO | WO 01/07444 A1 | 2/2001 |
| WO | WO 01/30304 A1 | 5/2001 |
| WO | WO 01/30305 A1 | 5/2001 |
| WO | WO 01/30306 A1 | 5/2001 |
| WO | WO 01/30307 A1 | 5/2001 |
| WO | WO 01/64129 A1 | 9/2001 |
| WO | WO 01/92271 A1 | 12/2001 |

OTHER PUBLICATIONS

Ciba Speciality Chemicals Coating Effects, "Ciba® CGI 403 Photoinitiator A Comparison of CGI 403 to Irgacure® 819," Ciba Specialty Chemicals Corporation, Tarrytown, NY, 5 pgs. (Feb. 8, 2001).

Lopes et al., "Effect of a new resin inlay/onlay restorative material on cuspal reinforcement," *Quintessence Int.*, vol. 22(8):641–645 (Aug., 1991).

Mathis et al., "Properties of a New Glass Ionomer/Composite Resin Hybrid Restorative," Abstract No. 51, *J. Dent Res.*, vol. 66:113 (no month indicated, 1987).

Morin et al., "Cusp Reinforcement by the Acid–etch Technique," *J. Dent Res.*, vol. 63(8):1075–1078 (Aug., 1984).

Morin et al., "Biophysical stress analysis of restored teeth: experimental strain measurement," *Dent Mater.*, vol. 4(1):41–48 (Feb., 1988).

Product Information Sheet, "3MConcise™ Restorative Material, Instructions for use" 3M Dental Products, St. Paul, MN, 1 pg. (Oct., 2000).

Product Information Sheet, "3M Filtek™ Z250 Universal Restorative, Instructions for use" 3M Dental Products, St. Paul, MN, 1 pg. (Nov., 1998).

Product Information Sheet, "3M Filtek™ Z250 Universal Restorative, Instructions for use" 3M Dental Products, St. Paul, MN, 1 pg. (Jan., 1999).

Product Information Sheet, "3M Single Bond Dental Adhesive System, Instructions for use" 3M Dental Products, St. Paul, MN, 2 pgs. (Feb., 2000).

Product Information Brochure, "The dual phase light curing for time saving cementing ESPE TULUX–CEM," German Product Information Brochure with translation, ESPE, Factory for Pharmaceutical Preparations GmbH & Co., Seefeld/Oberbayern, West Germany, 12 pgs. (no month or year indicated).

*Primary Examiner*—Cary E. O'Connor
(74) *Attorney, Agent, or Firm*—Sean J. Edman

(57) ABSTRACT

Processes for forming dental materials that include applying a hardenable dental adhesive to a surface and a second hardenable dental composite to the dental adhesive. The hardenable dental composite includes at least two adjacent regions with different concentrations of a photoinitiator, at least two adjacent regions with different photoinitiators, or both.

62 Claims, No Drawings

U.S. PATENT DOCUMENTS

| | | |
|---|---|---|
| 5,501,727 A | 3/1996 | Wang et al. |
| 5,520,725 A | 5/1996 | Kato et al. |
| 5,525,648 A | 6/1996 | Aasen et al. |
| 5,545,676 A | 8/1996 | Palazzotto et al. |
| 5,856,373 A | 1/1999 | Kaisaki et al. |
| 5,859,089 A | 1/1999 | Qian |
| 5,871,360 A | 2/1999 | Kato |
| 5,925,715 A | 7/1999 | Mitra |
| 5,962,550 A | 10/1999 | Akahane et al. |
| 5,965,632 A | 10/1999 | Orlowski et al. |
| 5,980,253 A | 11/1999 | Oxman et al. |
| 6,008,264 A | 12/1999 | Ostler et al. |
| 6,030,606 A | 2/2000 | Holmes |
| 6,043,295 A | 3/2000 | Oxman et al. |
| 6,084,004 A | 7/2000 | Weinmann et al. |
| 6,187,833 B1 | 2/2001 | Oxman et al. |
| 6,187,836 B1 | 2/2001 | Oxman et al. |
| 6,251,963 B1 | 6/2001 | Köhler et al. |
| 6,306,926 B1 | 10/2001 | Bretscher et al. |
| 6,353,041 B1 * | 3/2002 | Qian .......................... 523/116 |
| 6,387,981 B1 | 5/2002 | Zhang et al. |
| 2001/0032985 A1 | 10/2001 | Bhat et al. |
| 2002/0016378 A1 | 2/2002 | Jin et al. |
| 2003/0186197 A1 * | 10/2003 | Allred et al. ................ 433/226 |

* cited by examiner

US 6,773,261 B2

PROCESSES FOR FORMING DENTAL MATERIALS

TECHNICAL FIELD

This invention relates to processes for forming dental materials from hardenable dental compositions involving generally sequential hardening.

BACKGROUND

Hardenable polymeric materials are used in a wide variety of dental applications, including composites, filling materials, restoratives, cements, adhesives, and the like. Often, such materials shrink upon hardening. This is particularly problematic when the material is in a constrained environment, as in a dental filling or restorative, for example. Dimensional changes upon shrinkage while in a constrained environment can generate a strain within the material that is typically converted into a stress on the surrounding environment (e.g., tooth). Such forces can result in interfacial failures between the tooth and the polymeric material resulting in a physical gap and subsequent microleakage into the tooth cavity. Alternatively, such forces can lead to fractures within the tooth and/or the composite.

Generally, conventional processes of hardening polymeric dental materials involve a composite held in place on an oral surface with an adhesive and involve hardening the adhesive and then subsequently hardening the composite material. More specifically, conventional methods utilize one or more of the following steps: surface treatment of the tooth (e.g., etching, priming), application of a hardenable adhesive to the tooth surface, curing of the adhesive, placement of a composite material (e.g., restorative) on the hardened adhesive, and curing of the composite material. Such methods also typically utilize a blue light source emitting between approximately 380 nm to 520 nm to induce hardening.

Thus, there is a need for methods of hardening dental materials, e.g., dental adhesives and dental composites, that reduce the amount of stress placed on the dental material and the surrounding environment during or after hardening.

SUMMARY OF THE INVENTION

The present invention provides processes for hardening (e.g., curing by polymerization, crosslinking, ionic reaction, or other chemical reaction) hardenable compositions involving a generally sequential hardening of the compositions. Such processes are particularly useful in dental applications, such as dental sealants, dental adhesives, dental cements, dental composites, dental restoratives, and dental prostheses, for example. The processes of the present invention typically result in a reduction in the amount of stress placed on the dental material and surrounding environment during and/or after hardening of the material.

Generally, the processes of the present invention involve applying a radiation source and irradiating a hardenable dental composite that includes at least two adjacent regions with different concentrations of a photoinitiator, at least two adjacent regions with different photoinitiators, or both. Preferably, hardening of a region furthest from the radiation source is initiated first. These regions can be in the form of layers, although they do not necessarily need to be.

The dental composite is adhered to a surface through a dental adhesive that is in contact with a dental surface (e.g., tooth surface or bone). In certain embodiments, either while the dental composite is hardening (e.g., polymerizing) or after it is substantially completely hardened, the processes involve initiating hardening of a hardenable dental adhesive that is in contact with the dental composite and the surface. In certain embodiments, the dental adhesive can be partially or substantially completely hardened prior to applying a hardenable dental composite to it. Typically, hardening of the dental adhesive can be carried out through a chemical curing mechanism or a photopolymerization mechanism, for example.

In one embodiment, the present invention provides a process for forming a dental material adhered to a surface that includes: applying a hardenable dental adhesive to the surface; applying a hardenable dental composite to the hardenable dental adhesive on the surface, wherein the hardenable dental composite includes at least two adjacent regions with different concentrations of a photoinitiator; applying a radiation source to irradiate the hardenable dental composite, wherein hardening of a region furthest from the radiation source is initiated first; and hardening the hardenable dental adhesive to adhere the dental composite to the surface through the adhesive. In certain embodiments, the photoinitiator is a phosphine oxide and in others, the photoinitiator is a monoketone, a diketone, or a combination thereof.

In another embodiment, a process for forming a dental material adhered to an oral surface includes: applying a hardenable dental adhesive to the surface; at least partially hardening the hardenable dental adhesive; applying a hardenable dental composite to the at least partially hardened dental adhesive on the surface, wherein the hardenable dental composite includes at least two adjacent regions with different concentrations of a photoinitiator; and applying a radiation source to irradiate the hardenable dental composite and adhere it to the surface through the adhesive, wherein hardening of a region furthest from the radiation source is initiated first.

In yet another embodiment, a process for forming a dental material adhered to an oral surface includes: applying a hardenable dental adhesive to the surface; applying a hardenable dental composite to the hardenable dental adhesive on the surface, wherein the hardenable dental composite includes at least two adjacent regions with different photoinitiators; applying a radiation source to irradiate the hardenable dental composite; and hardening the hardenable dental adhesive to adhere the dental composite to the surface through the adhesive. Optionally, the hardenable dental composite can further include at least two adjacent regions of different concentrations of a photoinitiator. Preferably, hardening of a region furthest from the radiation source is initiated first.

In still another embodiment, a process for forming a dental material adhered to an oral surface includes: applying a hardenable dental adhesive to the surface; at least partially hardening the hardenable dental adhesive; applying a hardenable dental composite to the at least partially hardened dental adhesive on the surface, wherein the hardenable dental composite comprises at least two adjacent regions with different photoinitiators; and applying a radiation source to irradiate the hardenable dental composite and adhere it to the surface through the adhesive. Optionally, the hardenable dental composite can further include at least two adjacent regions of different concentrations of a photoinitiator. Preferably, hardening of a region furthest from the radiation source is initiated first.

Each of the above embodiments includes a hardenable dental composite that includes at least one photoinitiator. In contrast, the hardenable dental adhesive can include at least one photoinitiator or not.

DETAILED DESCRIPTION OF PREFERRED EMBODIMENTS

The present invention provides processes for forming dental materials adhered to a surface. The surface is typically an oral surface such as the surface of a tooth or a bone, although other surfaces are encompassed, such as the surface of a fixture used to prepare a prosthetic device, for example.

The dental materials can be used for example, as dental adhesives, artificial crowns, anterior or posterior fillings, casting materials, cavity liners, cements, coating compositions, mill blanks, restoratives, composites, prostheses, and sealants. In a preferred aspect, the dental material is a dental restorative. The restoratives of the invention can be placed directly in the mouth and cured (hardened) in situ.

The processes involve applying a radiation source and irradiating a hardenable dental composite that includes at least two adjacent regions with different concentrations of a photoinitiator, at least two adjacent regions with different photoinitiators, or both. Preferably, hardening of a region furthest from the radiation source is initiated first.

A hardenable dental adhesive can be hardened while the dental composite is hardening (e.g., polymerizing) or after the dental composite is substantially completely hardened, or even before a hardenable dental composite is applied to the dental adhesive. Typically, hardening of the dental adhesive can be carried out through a chemical curing mechanism or a photopolymerization mechanism, for example.

As used herein, a "substantially completely hardened" composition is one that is sufficiently hard to support a load that would typically be applied in a dental environment.

In certain embodiments, both the hardenable adhesive and composite compositions include photopolymerizable materials. In other embodiments, the adhesive composition is chemically hardenable. It is also envisioned that photopolymerizable materials and chemically hardenable materials can be combined in one composition if desired.

The hardenable compositions of the present invention include compounds that are monomers, oligomers, polymers, or combinations thereof. Such materials are well known for both photopolymerizable dental compositions as well as chemically hardenable dental compositions. Typical polymerizable composition may also contain suitable additives such as fluoride sources, anti-microbial agents, accelerators, stabilizers, absorbers, pigments, dyes, viscosity modifiers, surface tension depressants and wetting aids, antioxidants, fillers, and other ingredients well known to those skilled in the art. The amounts and types of each ingredient should be adjusted to provide the desired physical and handling properties before and after polymerization.

Generally, dental compositions include fillers of the types described herein below. Depending on the type of resin system in the composition, e.g., cationically curable resins, different types of fillers are used. Depending on the type of composition, e.g., adhesive, different amounts of fillers are used. Such information is generally known to one of skill in the art. For example, adhesives and sealants are generally lightly filled (e.g., up to about 25 wt-% filler, based on the total weight of the composition) or unfilled. Cements often contain higher amounts of filler (e.g., about 25 wt-% to about 60 wt-% filler, based on the total weight of filler), and filling materials can contain even higher amounts of filler (e.g., about 50 wt-% to about 90 wt-% filler, based on the total weight of the composition).

Photopolymerizable Compositions

The hardenable compositions used in the methods of the present invention are in certain embodiments photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. Preferably, the irradiation has a functional wavelength range from about 380 nm to about 520 nm.

Suitable photopolymerizable compositions may include epoxy resins (which contain cationically active epoxy groups), vinyl ether resins (which contain cationically active vinyl ether groups), and ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof. Also suitable are polymerizable materials that contain both a cationically active functional group and a free radically active functional group in a single compound. Examples include epoxy-functional acrylates, epoxy-functional methacrylates, and combinations thereof.

Free Radically Photopolymerizable Compositions

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bisacrylates and bis-methacrylates of polyethylene glycols of molecular weight 200–500, copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyl adipate and divinyl phthalate. Mixtures of two or more free radically polymerizable compounds can be used if desired.

Cationically Photopolymerizable Compositions

Photopolymerizable compositions may include compounds having cationically active functional groups such as cationically polymerizable epoxy resins. Such materials include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Suitable epoxy-containing materials useful in the present invention are listed in U.S. Pat. No. 6,187,836 (Oxman et al.) and U.S. Pat. No. 6,084,004 (Weinmann et al.).

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable compositions may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to about 200, intermediate molecular weights, i.e. from about 200 to about 10,000, or high molecular weights, i.e. above about 10,000. As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below about 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The amount of hydroxyl-containing organic material used in the polymerizable compositions may vary over broad ranges, depending upon factors such as the compatibility of the hydroxyl-containing material with the cationically and/or free radically polymerizable component, the equivalent weight and functionality of the hydroxyl-containing material, the physical properties desired in the final composition, the desired speed of polymerization, and the like.

Blends of various hydroxyl-containing materials may also be used. Examples of such blends include two or more molecular weight distributions of hydroxyl-containing compounds, such as low molecular weight (below about 200), intermediate molecular weight (about 200 to about 10,000) and higher molecular weight (above about 10,000). Alternatively, or additionally, the hydroxyl-containing material may contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The polymerizable material(s) may also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, and tri-(meth)acrylate, sorbitol mono-, di-, tri-, tetra-, or penta-(meth)acrylate; and 2,2-bis[4-(2-hydroxy-3-methacryloxypropoxy)phenyl]propane.

The polymerizable material(s) may also contain hydroxyl groups and cationically active functional groups in a single molecule. An example is a single molecule that includes both hydroxyl groups and epoxy groups.

Photoinitiators

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, and diphenyliodonium tetrafluoroboarate. Preferred photosensitizers are monoketones and diketones that absorb some light within a range of about 450 nm to about 520 nm (preferably, about 450 nm to about 500 nm). More preferred compounds are alpha diketones that have some light absorption within a range of about 450 nm to about 520 nm (even more preferably, about 450 to about 500 nm). Preferred compounds are camphorquinone, benzil, furil, 3,3,6,6-tetramethylcyclohexanedione, phenanthraquinone and other cyclic alpha diketones. Most preferred is camphorquinone. Preferred electron donor compounds include substituted amines, e.g., ethyl dimethylaminobenzoate.

Suitable photoinitiators for polymerizing cationically photopolymerizable compositions include binary and tertiary systems. Typical tertiary photoinitiators include an iodonium salt, a photosensitizer, and an electron donor compound as described in U.S. Pat. No. 5,856,373 (Kaisaki et al.), U.S. Pat. No. 6,084,004 (Weinmann et al.), U.S. Pat. No. 6,187,833 (Oxman et al.), and U.S. Pat. No. 6,187,836 (Oxman et al.); and in U.S. Ser. No. 10/050218 (Dede et al.; filed Jan. 15, 2002). Preferred iodonium salts, photosensitizers, and electron donor compounds are as listed herein for photoinitiator systems for polymerizing free radically photopolymerizable compositions.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Suitable acyl phosphine oxides have the general formula:

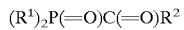
$(R^1)_2P(=O)C(=O)R^2$ wherein: each $R^1$ is individually is a hydrocarbyl group (e.g., alkyl, cycloalkyl, aryl, and aralkyl, any of which can be substituted with a halo, alkyl, or alkoxy group), wherein optionally two $R^1$ groups can be joined to form a ring along with the phosphorous atom; and each $R^2$ is independently a hydrocarbyl group, an S-, O-, or N-containing five- or six-membered heterocyclic group (aromatic or alicyclic), or a —Z—C(=O)P(=O)($R^1$)$_2$ group, wherein Z represents a divalent hydrocarbyl group such as alkylene or phenylene having from 2 to 6 carbon atoms.

Suitable bisacyl phosphine oxides have the general formula:

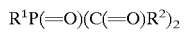
$R^1P(=O)(C(=O)R^2)_2$ wherein: $R^1$ is a hydrocarbyl group; and each $R^2$ is independently a hydrocarbyl group (e.g., alkyl, cycloalkyl, aryl, and aralkyl, any of which can be substituted with a halo, alkyl, or alkoxy group), an S-, O-, or N-containing five- or six-membered heterocyclic group (aromatic or alicyclic).

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4, 6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Preferred acyl phosphine oxides useful in the present invention are those in which the $R^1$ and $R^2$ groups are phenyl, C1-C4 alkyl, or C1-C4 alkoxy-substituted phenyl. Most preferably, the acyl phosphine oxide is bis(2,4,6-trimethylbenzoyl)phenyl phosphine oxide (IRGACURE 819, Ciba Specialty Chemicals).

Typically, the phosphine oxide initiator is present in the photopolymerizable composition in catalytically effective amounts, such as from about 0.1 weight percent to about 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from about 0.1 weight percent to about 5.0 weight percent, based on the total weight of the composition.

Photopolymerization Procedure

The photopolymerizable compositions are typically prepared by admixing, under "safe light" conditions (i.e., conditions that do not cause premature hardening of the composition), the various components of the compositions. Suitable inert solvents may be employed if desired when preparing the mixture. Examples of suitable solvents include acetone and dichloromethane.

Hardening is effected by exposing the composition to a radiation source, preferably a visible light source. It is convenient to employ light sources that emit visible light between 380 nm and 800 nm (particularly blue light of a wavelength of 380–520 nm) such as quartz halogen lamps, tungsten-halogen lamps, mercury arcs, carbon arcs, low-, medium-, and high-pressure mercury lamps, plasma arcs, light emitting diodes, and lasers. More preferred light sources include tungsten-halogen lamps, plasma arcs, and light-emitting diodes.

In general, useful light sources have intensities in the range of 200–1200 mW/Cm$^2$. One example, which is particularly useful for dental applications, is a XL-3000 dental curing light commercially available from 3M Company of St. Paul, Minn. Such lights have an intensity of about 400–800 mW/cm$^2$ within the wavelength region of 400–500 nm.

The exposure may be effected in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity.

Where dual exposures are employed, the intensity of each dosage may be the same or different. Similarly, the total energy of each exposure may be the same or different.

A variety of conventional lights for hardening such compositions can be used. Alternatively, the light described in Applicants' Assignee's copending U.S. patent application Ser. No. 10/185,431, filed on 28 Jun. 2002 can also be used.

Chemically Polymerizable Compositions

The hardenable compositions of the present invention are in certain embodiments, e.g., dental adhesive compositions, chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include glass ionomer cements, resin-modified glass ionomer cements, redox cure systems, and combinations thereof.

Glass Ionomer Cements

The chemically hardenable compositions may include conventional glass ionomers that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers typically are supplied in powder/liquid formulations that are mixed just before use. The mixture will undergo self-hardening in the dark due to an ionic reaction between the acidic repeating units of the polycarboxylic acid and cations leached from the glass.

Resin-Modified Glass Ionomer Cements

The chemically hardenable compositions may include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g. as described in U.S. Pat. No. U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Qrlowski et al.). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. patent Ser. No. 09/916,399 (Mitra; Filed Jul. 27, 2001).

Redox Cure Systems

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. patent Ser. No. 10/121,326 (Mitra et al.; Filed Apr. 12, 2002) and U.S. patent Ser. No. 10/121,329 (Mitra et al.; Filed Apr. 12, 2002).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. patent Ser. No. 10/121,329 (Mitra et al.; Filed Apr. 12, 2002).

The reducing and oxidizing agents are present in an amount sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least about 0.01 wt-%, and more preferably at least about 0.1 wt-%, based on the total weight (including water) of the components of the polymerizable composition. Preferably, the reducing agent is present in an amount of no greater than about 10 wt-%, and more preferably no greater than about 5 wt-%, based on the total weight (including water) of the components of the polymerizable composition.

Preferably, the oxidizing agent is present in an amount of at least about 0.01 wt-%, and more preferably at least about 0.10 wt-%, based on the total weight (including water) of the components of the polymerizable composition. Preferably, the oxidizing agent is present in an amount of no greater than about 10 wt-%, and more preferably no greater than about 5 wt-%, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g. with a glass ionomer cement and with a photopolymerizable composition such as described U.S. Pat. No. 5,154,762 (Mitra et al.).

The hardenable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

The hardenable compositions may also contain a combination of redox initiators and photoinitiators.

Fillers

The hardenable compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler is also substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

Preferably, the average particle size (typically, diameter) for the FAS glass is no greater than about 10 micrometers, and more preferably no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used either in the same part or in different parts.

Other suitable fillers are disclosed in U.S. Pat. No. 6,387,981 (Zhang et al.) as well as International Publication Nos. WO 01/30304 (Wu et al.), WO 01/30305 (Zhang et al.), WO 01/30306 (Windisch et al.), and WO 01/30307 (Zhang et al.).

U.S. Pat. No. 6,306,926 (Bretscher et al.) disclose a number of radiopacifying fillers that can be used in both free radically polymerizable compositions, cationically polymerizable compositions, and hybrid compositions featuring both free radically and cationically polymerizable components. They are particularly advantageous for use in cationically polymerizable compositions. One such filler is a melt-derived filler that includes 5–25% by weight aluminum oxide, 10–35% by weight boron oxide, 15–50% by weight lanthanum oxide, and 20–50% by weight silicon oxide. Another filler is a melt-derived filler that includes 10–30% by weight aluminum oxide, 10–40% by weight boron oxide, 20–50% by weight silicon oxide, and 15–40% by weight tantalum oxide. A third filler is a melt-derived filler that includes 5–30% by weight aluminum oxide, 5–40% by weight boron oxide, 0–15% by weight lanthanum oxide, 25–55% by weight silicon oxide, and 10–40% by weight zinc oxide. A fourth filler is a melt-derived filler that includes 15–30% by weight aluminum oxide, 15–30% by weight boron oxide, 20–50% by weight silicon oxide, and 15–40% by weight ytterbium oxide. A fifth filler is in the form of non vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or compound. A sixth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound.

Dental Adhesives

Numerous examples of hard tissue adhesives have been disclosed. For example, U.S. Pat. No. 4,719,149 (Aasen et al.) and references therein include a variety of materials and methods for adhering methacrylate-based composites to hard tissues. There are many other patents that describe various preferred materials and protocols for bonding to teeth, such as for example, U.S. Pat. No. 5,256,447 (Oxman et al.) and U.S. Pat. No. 5,525,648 (Aasen et al.). U.S. Pat. No. 5,980,253 (Oxman et al.) describes materials and methods for bonding cationically curable compositions to hard tissues.

Certain embodiments of the dental adhesives include at least one free radical inhibitor. The amount of inhibitor is sufficient to reduce the amount of cross-boundary polymerization. Examples include BHT (2,6-di-tert-butyl-4-methylphenol), MEHQ (methylethyl hydroquinone), and bisphenol-A. Typically, the inhibitor is used in an amount of about 0.05 wt-% to about 1.0 wt-%, based on the weight of the resin (e.g., adhesive composition without filler).

Such known materials can be used in the processes of the present invention. Generally, these materials have been used in processes that initially harden the adhesive and then the composite material. That is, conventional methods utilize one or more of the following steps: surface treatment of the tooth (e.g., etching, priming), application of a hardenable adhesive to the tooth surface, curing of the adhesive, placement of a composite material (e.g., restorative) on the hardened adhesive, and curing of the composite material.

Dental Composites

The composites of the present invention are generally considered to be highly filled compositions and are typically hardened (e.g., polymerized or cured) using either free radical and or cationic photoinitiator systems, e.g., the ternary photoinitiator systems described herein. When cured the composites are effective as filling or restorative materials to fill a hole, crack, or cavity, e.g., a cavity within a tooth.

Preferred composite materials include methacrylate and epoxy compositions as well as glass ionomers that include polyacrylic acids, water, FAS glasses, and optionally free radically polyermizable resins and polymerization catalysts such as described in U.S. Pat. No. 6,306,926 (Bretscher et al.) and U.S. Pat. No. 6,030,606 (Holmes).

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

| Abbreviations, Descriptions, and Sources of Materials | | |
| --- | --- | --- |
| Abbreviation | Description | Source |
| Bis-GMA | 2,2-Bis[4-(2-hydroxy-3-methacryloxy-propoxy)phenyl]propane | CAS No. 1565-92-2 |
| EDMAB | Ethyl 4-dimethylaminobenzoate | Sigma-Aldrich (St. Louis, MO) |
| CPQ | Camphorquinone visible light sensitizer | Sigma-Aldrich |
| IRGACURE 819 | Phosphine oxide initiator | Ciba Specialty Chemicals Corp., Terrytown, NY |
| AEROSIL R202 | Fumed silica | Degussa Corp., Akron, OH |
| DPI HFP | Diphenyliodonium hexafluorophosphate | Johnson Matthey, Alpha Aesar Division, Ward Hill, NJ |
| TEGDMA | Triethylene glycol dimethacrylate | Sartomer Co., West Chester, PA |

Example 1

Selective Curing of Layered Compositions Having Different Photoinitiators

The objective of this example was to demonstrate the physical differences between selectively cured layered compositions having different photoinitiator systems in different layers following sequential irradiation at different effective wavelength ranges.

Three resins were prepared by combining a 50/50 weight-% blend of bis-GMA/TEGDMA with following photoinitiator systems:

| | |
| --- | --- |
| Resin 1: | 0.5% CPQ, 0.5% DPI HFP, 0.5% EDMAB |
| Resin 2: | 0.5% IRGACURE 819 |
| Resin 3: | 50/50 weight-% blend of Resin 1 and Resin 2 |

Each of the above resins was filled with 10% AEROSIL R202 fumed silica to form very low viscosity compositions, designated Composition A, Composition B, and Composition C, respectively.

The three compositions were then layered and cured as follows within three different Teflon molds having cylindrical cavities (8-mm deep×6-mm diameter):

Mold A. Filled only with Composition A (CPQ sensitizer) and irradiated for 30 seconds with an ACCUCURE 3000 laser (Lasermed, Salt Lake City, Utah; about 460–500 nm effective wavelength) to cure the composition.

Mold B. Filled at the bottom 4 mm of the cavity with Composition A (CPQ sensitizer) and at the top 4 mm with Composition B (IRGACURE 819 initiator). The mold was irradiated for 30 seconds with the ACCUCURE 3000 laser to cure the Composition A layer (through the Composition B layer that remained uncured). The mold was then irradiated for 30 seconds with a VISILUX 2 halogen light (3M Company, St. Paul, Minn.; about 400–500 nm effective wavelength range) to cure the Composition B layer.

Mold C. Filled at the bottom 2 ⅔ mm of the cavity with Composition A (CPQ sensitizer), the center 2 ⅔ mm with Composition C (CPQ and IRGACURE 819) and the top 2 ⅔ mm with Composition B (IRGACURE 819 initiator). The filled mold was irradiated for 30 seconds with the ACCUCURE 3000 laser followed by irradiation for 30 seconds with the VISILUX 2 halogen light to sequentially cure the composition layers as in Mold B from bottom to top. The compositions were all cured following irradiation with the halogen light.

Following irradiation of Molds A–C, the cured compositions (designated cured Samples A–C, respectively) were removed from the molds and the following observations were made:

1. Composition A in Mold A was cured from the top down in a single irradiation step and following cure provided Sample A that exhibited slight concavity on the top surface and significant concavity on the bottom surface.
2. The composition layers in Molds B and C were cured sequentially from the bottom layer to the top layer as described above. Following cure, in direct contrast to Sample A, the Samples B and C exhibited slight concavity on the bottom surface and significant concavity on the top surface.

In this Example it is noted that the composition layers that cured in the TEFLON molds were not constrained in any dimension by adhesion to an interface and, therefore, it was possible to observe and assess the directional shrinkage associated with curing from the top-down or from the bottom-up following selective curing with different wavelength ranges of light. This can be very significant in practical applications, e.g., in dental restorative procedures. It is concluded from these observations that in conventional "top-down" curing of compositions, the bottom layer becomes constrained first and would tend to shrink away from a tooth surface thereby leading to stress build-up in the restoration. In contrast, utilization of "bottom-up" curing would permit shrinkage of the first-cured lower layer at the interface of the hardening lower layer and the still fluid upper layer, and subsequently would permit shrinkage of the second-cured upper layer at the unconstrained upper surface. This latter curing sequence would minimize constrained shrinkage thereby leading to a minimization of stress build-up in the restoration.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A process for forming a dental material adhered to a surface, the process comprising:
    applying a hardenable dental adhesive to the surface;
    applying a hardenable dental composite to the hardenable dental adhesive on the surface, wherein the hardenable dental composite comprises at least two adjacent regions with different concentrations of a photoinitiator;
    applying a radiation source to irradiate the hardenable dental composite, wherein hardening of a region furthest from the radiation source is initiated first; and
    hardening the hardenable dental adhesive to adhere the dental composite to the surface through the adhesive.
2. The process of claim 1 wherein hardening the hardenable dental adhesive comprises irradiating the hardenable dental adhesive.
3. The process of claim 2 wherein hardening the hardenable dental adhesive is initiated after the hardenable composite is substantially completely hardened.
4. The process of claim 2 wherein the hardenable dental adhesive comprises a photoinitiator that absorbs radiation within a range of about 380 nm to about 520 nm.
5. The process of claim 4 wherein the photoinitiator of the hardenable dental adhesive is a phosphine oxide.
6. The process of claim 1 wherein the photoinitiator absorbs radiation within a range of about 380 nm to about 520 nm.
7. The process of claim 6 wherein the photoinitiator is a phosphine oxide.
8. The process of claim 7 wherein the phosphine oxide is a bisacyl phosphine oxide of the general formula:

$$R^1P(=O)(C(=O)R^2)_2$$

wherein:
    $R^1$ is a hydrocarbyl group; and
    each $R^2$ is independently a hydrocarbyl group, an S-, O-, or N-containing five- or six-membered heterocyclic group.
9. The process of claim 6 wherein the photoinitiator comprises a monoketone, diketone, or combination thereof.
10. The process of claim 9 wherein the photoinitiator is selected from the group consisting of camphorquinone, benzil, furil, 3,3,6,6-tetramethylcyclohexanedione, phenanthraquinone, and combinations thereof.
11. The process of claim 1 wherein applying a radiation source to irradiate the hardenable dental composite occurs prior to hardening the hardenable dental adhesive to adhere the dental composite to the surface.
12. The process of claim 1 wherein hardening the hardenable dental adhesive occurs prior to applying a radiation source to irradiate the hardenable dental composite.
13. The process of claim 1 wherein the surface is an oral surface.
14. The process of claim 1 wherein the hardenable dental composite comprises a concentration gradient of the photoinitiator.
15. The process of claim 1 wherein the hardenable compositions comprise a free radically polymerizable composition, a cationically polymerizable composition, or combinations thereof.
16. The process of claim 1 wherein at least one of the hardenable compositions further comprises a filler.
17. A process for forming a dental material adhered to a surface, the process comprising:
    applying a hardenable dental adhesive to the surface;

at least partially hardening the hardenable dental adhesive;

applying a hardenable dental composite to the at least partially hardened dental adhesive on the surface, wherein the hardenable dental composite comprises at least two adjacent regions with different concentrations of a photoinitiator; and applying a radiation source to irradiate the hardenable dental composite and adhere it to the surface through the adhesive, wherein hardening of a region furthest from the radiation source is initiated first.

18. The process of claim 17 wherein hardening the hardenable dental adhesive comprises irradiating the hardenable dental adhesive.

19. The process of claim 18 wherein the hardenable dental adhesive comprises a photoinitiator that absorbs radiation within a range of about 380 nm to about 520 nm.

20. The process of claim 19 wherein the photoinitiator of the hardenable dental adhesive is a phosphine oxide.

21. The process of claim 17 wherein the photoinitiator absorbs radiation within a range of about 380 nm to about 520 nm.

22. The process of claim 21 wherein the photoinitiator is a phosphine oxide.

23. The process of claim 22 wherein the phosphine oxide is a bisacyl phosphine oxide of the general formula:

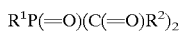

wherein:
R$^1$ is a hydrocarbyl group; and
each R$^2$ is independently a hydrocarbyl group, an S-, O-, or N-containing five- or six-membered heterocyclic group.

24. The process of claim 21 wherein the photoinitiator comprises a monoketone, diketone, or combination thereof.

25. The process of claim 24 wherein the photoinitiator is selected from the group consisting of camphorquinone, benzil, furil, 3,3,6,6-tetramethylcyclohexanedione, phenanthraquinone, and combinations thereof.

26. The process of claim 17 wherein the dental adhesive is substantially completely hardened prior to applying the hardenable dental composite.

27. The process of claim 17 wherein the surface is an oral surface.

28. The process of claim 17 wherein the hardenable dental composite comprises a concentration gradient of the photoinitiator.

29. The process of claim 17 wherein the hardenable compositions comprise a free radically polymerizable composition, a cationically polymerizable composition, or combinations thereof.

30. The process of claim 17 wherein at least one of the hardenable compositions further comprises a filler.

31. A process for forming a dental material adhered to a surface, the process comprising:

applying a hardenable dental adhesive to the surface;

applying a hardenable dental composite to the hardenable dental adhesive on the surface, wherein the hardenable dental composite comprises at least two adjacent regions with different photoinitiators;

applying a radiation source to irradiate the hardenable dental composite; and hardening the hardenable dental adhesive to adhere the dental composite to the surface through the adhesive.

32. The process of claim 31 wherein hardening the hardenable dental adhesive comprises irradiating the hardenable dental adhesive.

33. The process of claim 32 wherein hardening the hardenable dental adhesive is initiated after the hardenable composite is substantially completely hardened.

34. The process of claim 32 wherein the hardenable dental adhesive comprises a photoinitiator that absorbs radiation within a range of about 380 nm to about 520 nm.

35. The process of claim 34 wherein the photoinitiator of the hardenable dental adhesive is a phosphine oxide.

36. The process of claim 31 wherein the at least two different photoinitiators of the hardenable dental composite absorb radiation within a range of about 380 nm to about 520 nm.

37. The process of claim 36 wherein at least one of the photoinitiators of the hardenable dental composite is a phosphine oxide.

38. The process of claim 37 wherein the phosphine oxide is a bisacyl phosphine oxide of the general formula:

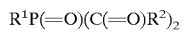

wherein:
R$^1$ is a hydrocarbyl group; and
each R$^2$ is independently a hydrocarbyl group, an S-, O-, or N-containing five- or six-membered heterocyclic group.

39. The process of claim 36 wherein at least one of the photoinitiators of the hardenable dental composite is a monoketone, diketone, or combination thereof.

40. The process of claim 39 wherein at least one of the photoinitiators of the hardenable dental composite is selected from the group consisting of camphorquinone, benzil, furil, 3,3,6,6-tetramethylcyclohexanedione, phenanthraquinone, and combinations thereof.

41. The process of claim 31 wherein applying a radiation source to irradiate the hardenable dental composite occurs prior to hardening the hardenable dental adhesive to adhere the dental composite to the surface.

42. The process of claim 31 wherein hardening the hardenable dental adhesive occurs prior to applying a radiation source to irradiate the hardenable dental composite.

43. The process of claim 31 wherein the surface is an oral surface.

44. The process of claim 31 wherein the hardenable dental composite further comprises at least two adjacent regions of different concentrations of a photoinitiator.

45. The process of claim 31 wherein the hardenable compositions comprise a free radically polymerizable composition, a cationically polymerizable composition, or combinations thereof.

46. The process of claim 31 wherein at least one of the hardenable compositions further comprises a filler.

47. The process of claim 31 wherein hardening of a region furthest from the radiation source is initiated first.

48. A process for forming a dental material adhered to a surface, the process comprising:

applying a hardenable dental adhesive to the surface;

at least partially hardening the hardenable dental adhesive;

applying a hardenable dental composite to the at least partially hardened dental adhesive on the surface, wherein the hardenable dental composite comprises at least two adjacent regions with different photoinitiators; and applying a radiation source to irradiate the hardenable dental composite and adhere it to the surface through the adhesive.

49. The process of claim 48 wherein hardening the hardenable dental adhesive comprises irradiating the hardenable dental adhesive.

50. The process of claim 49 wherein the hardenable dental adhesive comprises a photoinitiator that absorbs radiation within a range of about 380 nm to about 520 nm.

51. The process of claim 50 wherein the photoinitiator of the hardenable dental adhesive is a phosphine oxide.

52. The process of claim 48 wherein at least one of the photoinitiators of the hardenable dental composite absorbs radiation within a range of about 380 nm to about 520 nm.

53. The process of claim 52 wherein at least one of the photoinitiators of the hardenable dental composite is a phosphine oxide.

54. The process of claim 53 wherein the phosphine oxide is a bisacyl phosphine oxide of the general formula:

$$R^1P(=O)(C(=O)R^2)_2$$

wherein:

R$^1$ is a hydrocarbyl group; and each R$^2$ is independently a hydrocarbyl group, an S-, O-, or N-containing five- or six-membered heterocyclic group.

55. The process of claim 50 wherein at least one of the photoinitiators of the hardenable dental composite comprises a monoketone, diketone, or combination thereof.

56. The process of claim 55 wherein at least one of the photoinitiators of the hardenable dental composite is selected from the group consisting of camphorquinone, benzil, furil, 3,3,6,6-tetramethylcyclohexanedione, phenanthraquinone, and combinations thereof.

57. The process of claim 48 wherein the dental adhesive is substantially completely hardened prior to applying the hardenable dental composite.

58. The process of claim 48 wherein the surface is an oral surface.

59. The process of claim 48 wherein the hardenable dental composite further comprises at least two adjacent regions of different concentrations of a photoinitiator.

60. The process of claim 48 wherein the hardenable compositions comprise a free radically polymerizable composition, a cationically polymerizable composition, or combinations thereof.

61. The process of claim 48 wherein at least one of the hardenable compositions further comprises a filler.

62. The process of claim 48 wherein hardening of a region furthest from the radiation source is initiated first.

* * * * *

UNITED STATES PATENT AND TRADEMARK OFFICE
CERTIFICATE OF CORRECTION

PATENT NO. : 6,773,261 B2
DATED : August 10, 2004
INVENTOR(S) : Craig, Bradley D.

It is certified that error appears in the above-identified patent and that said Letters Patent is hereby corrected as shown below:

Column 8,
Line 46, delete "mW/Cm$^2$" and insert in place therefor -- mW/cm$^2$ --

Column 9,
Line 38, delete "Glass ionomer" and insert in place therefor -- Glass Ionomer --.

Column 14,
Line 26, delete "1565-92-2" and insert in place therefor -- 1565-94-2 --.

Signed and Sealed this

Eighth Day of February, 2005

JON W. DUDAS
*Director of the United States Patent and Trademark Office*